(12) United States Patent
Wang

(10) Patent No.: US 12,714,324 B2
(45) Date of Patent: Aug. 25, 2026

(54) METHOD FOR MEASURING VASCULAR STATE AND ADHESIVE VASCULAR STATE MEASUREMENT DEVICE THEREOF

(71) Applicant: NATIONAL TSING HUA UNIVERSITY, Hsinchu City (TW)

(72) Inventor: Ting-Wei Wang, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 241 days.

(21) Appl. No.: 18/636,810

(22) Filed: Apr. 16, 2024

(65) Prior Publication Data

US 2024/0398345 A1 Dec. 5, 2024

(30) Foreign Application Priority Data

May 31, 2023 (TW) ................................ 112120354

(51) Int. Cl.

| | |
|---|---|
| ***A61B 5/0265*** | (2006.01) |
| ***A61B 5/00*** | (2006.01) |
| ***A61B 5/02*** | (2006.01) |
| ***A61B 5/257*** | (2021.01) |

(52) U.S. Cl.

CPC ........ *A61B 5/0265* (2013.01); *A61B 5/02007* (2013.01); *A61B 5/257* (2021.01); *A61B 5/6832* (2013.01)

(58) Field of Classification Search

CPC ..... A61B 5/026; A61B 5/0263; A61B 5/0265; A61B 5/0285; A61B 5/0295

USPC ........................................ 600/504, 506, 507

See application file for complete search history.

(56) References Cited

U.S. PATENT DOCUMENTS 3,560,845 A * 2/1971 Goldberg ................. G01B 7/32 324/243
4,621,234 A * 11/1986 Caprihan ............... A61B 5/026 324/306
5,309,916 A * 5/1994 Hatschek ........... A61B 5/02125 600/452
5,642,734 A * 7/1997 Ruben .................... G01N 33/49 600/506

(Continued)

FOREIGN PATENT DOCUMENTS

CN 103006185 A 4/2013
CN 108879995 A 11/2018

(Continued)

*Primary Examiner* — Adam J Eiseman
(74) *Attorney, Agent, or Firm* — Birch, Stewart, Kolasch & Birch, LLP

(57) ABSTRACT

The method for measuring vascular state comprising: outputting a first transmission electromagnetic signal to a first detecting location of a target vessel, and outputting a second transmission electromagnetic signal to a second detecting location of the target vessel; receiving a first feedback electromagnetic signal induced, at the first detecting location, by the first transmission electromagnetic signal, and receiving a first feedback electromagnetic signal induced, at the first detecting location, by the first transmission electromagnetic signal; determining a signal characteristic difference between the first feedback electromagnetic signal and the second feedback electromagnetic signal; and determining at least one vascular state of the target vessel according to the signal characteristic difference.

13 Claims, 4 Drawing Sheets

(56) References Cited

U.S. PATENT DOCUMENTS

| | | | | |
|---|---|---|---|---|
| 5,935,077 | A * | 8/1999 | Ogle | A61B 5/0265 73/861.12 |
| 11,806,123 | B2 * | 11/2023 | Hartwell | A61B 5/0536 |
| 2003/0062891 | A1 * | 4/2003 | Slates | G01D 5/2053 324/207.26 |
| 2009/0137900 | A1 * | 5/2009 | Bonner | A61B 5/06 600/424 |
| 2009/0306524 | A1 * | 12/2009 | Muhlsteff | A61B 5/021 600/502 |
| 2010/0219841 | A1 * | 9/2010 | Feldkamp | A61B 5/02007 324/654 |
| 2010/0222696 | A1 * | 9/2010 | Feldkamp | A61B 5/0522 600/547 |
| 2012/0150458 | A1 * | 6/2012 | Sodickson | G01R 33/1215 702/57 |
| 2015/0045650 | A1 * | 2/2015 | Srinivasa | A61B 5/0265 600/409 |
| 2016/0169838 | A1 | 6/2016 | Nagarkar et al. | |
| 2018/0143150 | A1 | 5/2018 | Bezemer et al. | |
| 2019/0240486 | A1 * | 8/2019 | Simon | A61N 1/36025 |
| 2019/0336014 | A1 * | 11/2019 | Peeters | A61B 5/05 |
| 2019/0374127 | A1 * | 12/2019 | Feldkamp | A61B 5/72 |
| 2022/0160254 | A1 * | 5/2022 | Shahrestani | A61B 5/0816 |

FOREIGN PATENT DOCUMENTS

| | | | | |
|---|---|---|---|---|
| CN | 109745020 | A | 5/2019 | |
| CN | 110430803 | A | 11/2019 | |
| CN | 111772801 | A | 10/2020 | |
| JP | 2008-506444 | A | 3/2008 | |
| JP | 2019-170436 | A | 10/2019 | |
| TW | 200724094 | A | 7/2007 | |
| TW | 201907862 | A | 3/2019 | |
| WO | WO-2018108850 | A1 * | 6/2018 | A61B 5/05 |
| WO | WO 2020/209662 | A1 | 10/2020 | |
| WO | WO 2022/170263 | A2 | 8/2022 | |

* cited by examiner

FIG. 1

METHOD FOR MEASURING VASCULAR STATE AND ADHESIVE VASCULAR STATE MEASUREMENT DEVICE THEREOF

TECHNICAL FIELD

The present disclosure relates to a method for measuring vascular state and an adhesive vascular state measurement device. In particular, the present disclosure relates to a method for measuring vascular state and an adhesive vascular state measurement device that emits two sets of electromagnetic signals to two positions of a target vessel.

BACKGROUND

With the growth of population, the changes in dietary habits and irregular lifestyles, people become prone to accumulating fat or other impurities in blood vessels. When a blood vessel accumulates too much fat or other impurities that cannot be metabolized, the occlusion of the blood vessel and/or other situations may occur. The non-metabolized fat or other impurities will be aggregated and formed into plaques inside the blood vessel. The plaques will cause the blood vessel narrower to affect the blood supply function of the blood vessel. The deterioration procedure and situation of the blood vessel mentioned above is known as vascular stenosis. On the other hand, the blood vessel becomes prone to loss elasticity due to overweight and bad habits such as smoking or oily and salty diet, known as arteriosclerosis. The vascular stenosis or arteriosclerosis will accelerate systemic aging and become the main cause of various fatal diseases. In particular, the carotid artery stenosis is the most dangerous condition of the vascular stenosis. More specifically, the carotid artery stenosis is an invisible killer that leads to stroke. In a narrowed carotid artery, the blood flow velocity is accelerated and causes turbulence in the blood vessel. The turbulence of blood will increase the probability of thrombus formation, which will lead to ischemic stroke.

The vascular stenosis and arteriosclerosis are chronic vascular diseases, and patients may not have illness or feel the condition worsen in their daily lives. An ultrasound device is often used in clinical practice to regularly track and monitor vascular stenosis and arteriosclerosis for early evaluation and diagnosis of vascular stenosis and arteriosclerosis. For example, an ultrasound device for scanning neck can be used to track the vascular state of the carotid artery. However, ultrasound devices are large-scale medical instruments that are not easily promoted to small clinics or used for daily measurements. Besides, operators of the ultrasound devices need professional training. Therefore, the ultrasound devices cannot achieve the goal of real-time monitoring of the state of the blood vessels. In clinical, if symptoms or illness appear and then being detected by ultrasound device, it is likely to be severe vascular embolism or sclerosis, and the best treatment opportunity has been missed.

Therefore, vascular evaluation methods and devices that can be easily worn and even promoted for home care will be the focus issue in this field.

SUMMARY

One of the objects of the present disclosure is to provide a wearable adhesive vascular state measurement device.

One of the objects of the present disclosure is to provide a low-cost and portable method for measuring the state of blood vessels.

The present disclosure provides a method for measuring vascular state. The method comprising: outputting a first transmission electromagnetic signal to a first detecting location of a target vessel, and outputting a second transmission electromagnetic signal to a second detecting location of the target vessel; receiving a first feedback electromagnetic signal induced, at the first detecting location, by the first transmission electromagnetic signal, and receiving a second feedback electromagnetic signal induced, at the second detecting location, by the second transmission electromagnetic signal; determining a signal characteristic difference between the first feedback electromagnetic signal and the second feedback electromagnetic signal; and determining at least one vascular state of the target vessel according to the signal characteristic difference.

The present disclosure provides an adhesive vascular state measurement device. The adhesive vascular state measurement device comprises a flexible substrate, a first coil, a second coil and a control module. The flexible substrate is configured to being attached on a skin surface along a target vessel. The first coil is arranged at a first position of the flexible substrate. Wherein the first coil is configured to output a first transmission electromagnetic signal toward a first detecting location of the target vessel, and receive a first feedback electromagnetic signal induced, at the first detecting location, by the first transmission electromagnetic signal to generate a first sensing signal. The second coil is arranged at a second position of the flexible substrate. Wherein the second coil is configured to output a second transmission electromagnetic signal toward a second detecting location of the target vessel, and receive a second feedback electromagnetic signal induced, at the second detecting location, by the second transmission electromagnetic signal to generate a second sensing signal. The control module coupled with the first coil and the second coil. The control module includes a signal generating unit and a measurement unit. The signal generating unit is configured to generate an AC signal provided to the first coil and the second coil to generate the first transmission electromagnetic signal and the second transmission electromagnetic signal, respectively. The measurement unit is configured to receive the first sensing signal and the second sensing signal, and determine at least one vascular state of the target vessel according to a signal characteristic difference between the first sensing signal and the second sensing signal.

The method for measuring vascular state and the adhesive vascular state measurement device of the present disclosure can emit two sets of electromagnetic signals at two positions of the target vessel and receive feedback electromagnetic signals generated at two positions of the target vessel. By comparing the signal differences of individual feedback electromagnetic signals at two positions of the target vessel, the vascular state between the two positions of the target vessel can be estimated. Compared to ultrasound or other measurement methods, the method for measuring vascular state and the adhesive vascular state measurement device of the present disclosure can be made through circuits and circuit substrates, and the cost can be greatly reduced. In addition, electronic wearing devices are far more convenient and comfortable for portability and wearing than ultrasound-based measurement means. Therefore, it is possible to achieve real-time monitoring of vascular state at lower costs.

BRIEF DESCRIPTION OF THE DRAWINGS

The accompanying drawings are presented to help describe various aspects of the present disclosure. In order to simplify the accompanying drawings and highlight the contents to be presented in the accompanying drawings, conventional structures or elements in the accompanying drawings may be drawn in a simple schematic way or may be omitted. For example, a number of elements may be singular or plural. These accompanying drawings are provided merely to explain these aspects and not to limit them.

FIG. 1 is a flowchart of a method for measuring vascular state according to the first embodiment of the present disclosure.

DETAILED DESCRIPTION

Any reference to elements using terms such as "first" and "second" herein generally does not limit the number or order of these elements. Conversely, these names are used herein as a convenient way to distinguish two or more elements or element instances. Therefore, it should be understood that the terms "first" and "second" in the request item do not necessarily correspond to the same names in the written description. Furthermore, it should be understood that references to the first element and the second element do not indicate that only two elements can be used or that the first element needs to precede the second element. Open terms such as "include", "comprise", "have", "contain", and the like used herein means including but not limit to.

The term "coupled" is used herein to refer to direct or indirect electrical coupling between two structures. For example, in an example of indirect electrical coupling, one structure may be coupled with another structure through a passive element such as a resistor, a capacitor, or an inductor.

In the present disclosure, the term such as "exemplary" or "for example" is used to represent "giving an example, instance, or description". Any implementation or aspect described herein as "exemplary" or "for example" is not necessarily to be construed as preferred or advantageous over other aspects of the present disclosure. The terms "about" and "approximately" as used herein with respect to a specified value or characteristic are intended to represent within a value (for example, 10%) of the specified value or characteristic.

First Embodiment

Figure 1:
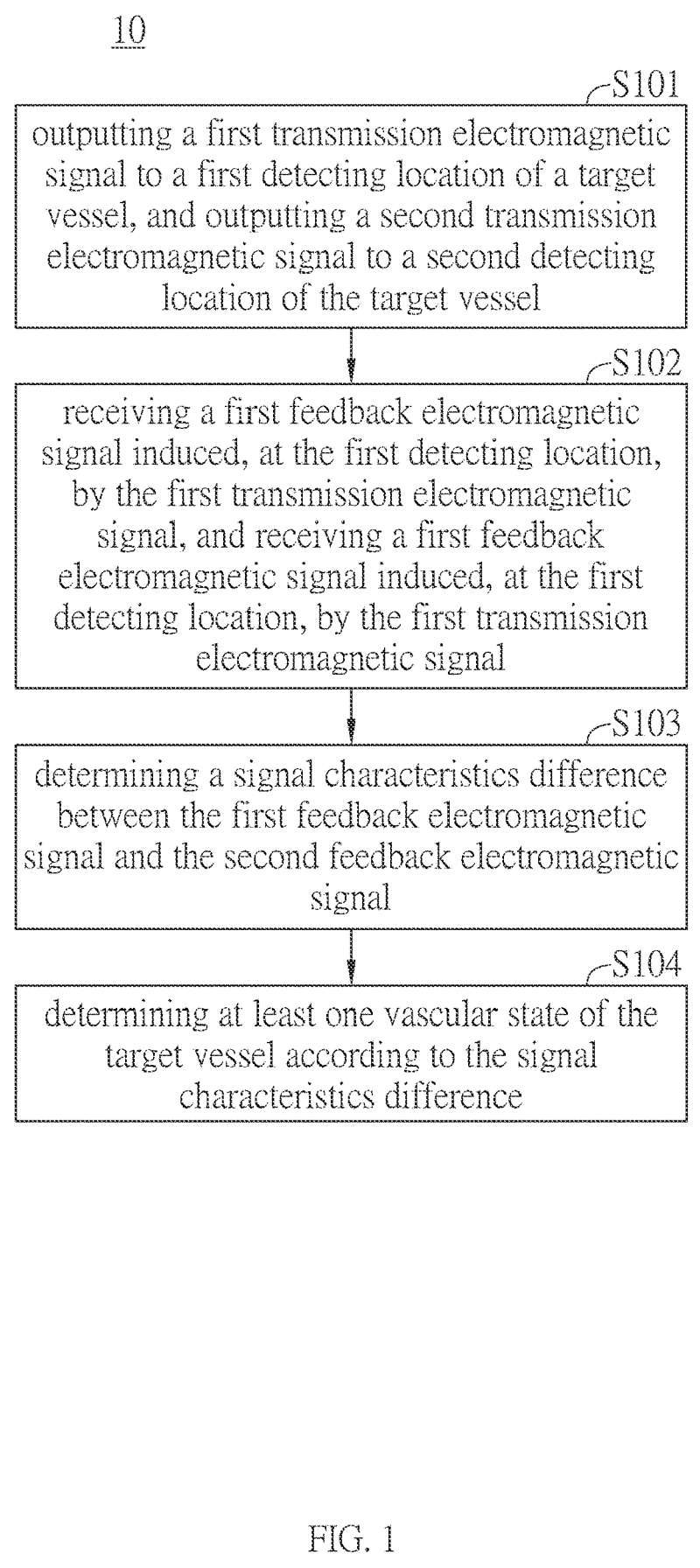

Referring FIG. 1, FIG. 1 illustrates the flow chart of the method for measuring vascular state 10. The method for measuring vascular state comprising: (step S101) outputting a first transmission electromagnetic signal to a first detecting location of a target vessel, and outputting a second transmission electromagnetic signal to a second detecting location of the target vessel; (step S102) receiving a first feedback electromagnetic signal induced, at the first detecting location, by the first transmission electromagnetic signal, and receiving a first feedback electromagnetic signal induced, at the first detecting location, by the first transmission electromagnetic signal; (step S103) determining a signal characteristic difference between the first feedback electromagnetic signal and the second feedback electromagnetic signal; and (step S104) determining at least one vascular state of the target vessel according to the signal characteristic difference.

Figure 2:
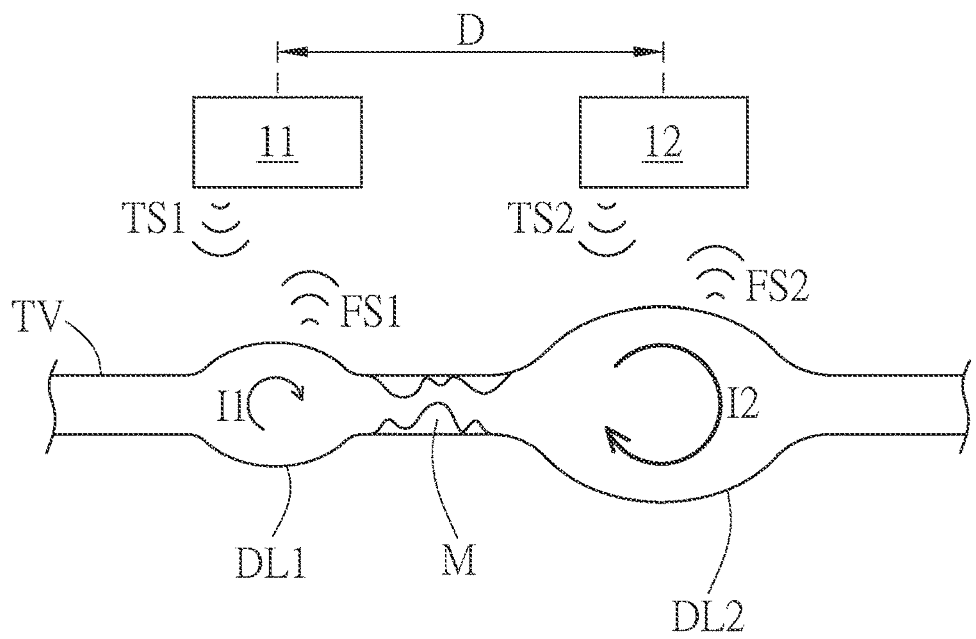
FIG. 2 is a schematic diagram of a method for measuring vascular state according to the first embodiment of the present disclosure.

More specifically, referring to FIG. 2, FIG. 2 illustrates a schematic diagram of the method for measuring vascular state 10 of the present disclosure. As shown in FIG. 2, in step (S101), the first transmission electromagnetic signal (TS1) can be output to the first detecting location (DL1) of the target vessel (TV) through the radiation emission components 11 and 12 (e.g. coils), and the second transmission electromagnetic signal (TS2) can be transmitted to the second detecting location (DL2) of the target vessel (TV). The radiation emission components 11 and 12 can be coupled to, for example, signal generators or frequency signal generating circuits. Accordingly, the radiation emission components 11 and 12 will receive high-frequency electrical signals and convert the electrical signals into the first transmission electromagnetic signal (TS1) and the second transmission electromagnetic signal (TS2). It should be noted that the present invention does not limit the frequency of the first transmission electromagnetic signal (TS1) and the second transmission electromagnetic signal (TS2). In an embodiment, the frequency of the first transmission electromagnetic signal (TS1) and the second transmission electromagnetic signal (TS2) ranges, preferably, from 1 MHz to 10 MHz, which provides better penetration depth and resolution for detecting surface blood vessels. However, the frequencies of the first transmission electromagnetic signal (TS1) and the second transmission electromagnetic signal (TS2) can be adjusted based on the required measurement depth and resolution of the target vessel (TV).

After the first electromagnetic signal (TS1) and the second electromagnetic signal (TS2) are transmitted, respectively, to the first detecting location (DL1) and the second detecting location (DL2) of the target vessel (TV), each of the first detecting location (DL1) and the second detecting location (DL2) of the target vessel (TV) can be considered as a planar conductor. Therefore, the first electromagnetic signal (TS1) and the second electromagnetic signal (TS2) induce the first detecting location (DL1) and the second detecting location (DL2), respectively, and generate the eddy current (11) and the eddy current (12) at the first detecting location (DL1) and the second detecting location (DL2) of the target vessel (TV), correspondingly. It should be noted that the amplitude, frequency, and/or difference of generating time of the eddy current (11) and the eddy current (12) may be varied depending on the vascular state at the first detecting location (DL1) and the second detecting location (DL2). For example, when there is a fat accumulation or thrombus (M) between the first detecting location (DL1) and the second detecting location (DL2) causing embolism or vessel narrow, the blood flow pressure at the first detecting location (DL1) and the second detecting location (DL2) will be different. The difference of blood pressures will result in different levels of contraction/relaxation of the target vessel (TV) at the first detecting location (DL1) and the second detecting location (DL2), and affect the amplitude of the eddy current (11) and the eddy current (12). In another example, the pulse wave velocity (PWV) within the target vessel (TV) may also affect the difference of generating time of the eddy currents (11) and (12). More specifically, the time difference of the contraction/relaxation caused by pulse propagation between the first detecting location (DL1) and the second detecting location (DL2) of the target vessel (TV) will result in a time difference between the generation of the eddy currents (11) and (12). The eddy currents (11) and (12) induced at the first detecting location (DL1) and the second detecting location (DL2) of the target vessel (TV) will generate the first feedback electromagnetic signal (FS1) and second feedback electromagnetic signal (FS2). The difference in signal characteristics (e.g. frequency, or peak time difference) between the first feedback electromagnetic signal (FS1) and the second feedback electromagnetic signal (FS2) will be varied due to the difference in the eddy currents (11) and (12).

In step (S102), the first feedback electromagnetic signal (FS1) and the second feedback electromagnetic signal (FS2) can be received by the radiation emission components 11 and 12. The first feedback electromagnetic signal (FS1) and the second feedback electromagnetic signal (FS2) will be converted, by an analog conversion or a digital conversion, into electrical signals for facilitating the following signal processing procedure(s). It should be noted that in step S102 of the present disclosure, the reception of the first feedback electromagnetic signal (FS1) and the second feedback electromagnetic signal (FS2) is not limited to the radiation emission components 11 and 12 that emit the first transmission electromagnetic signal (TS1) and the second transmission electromagnetic signal (TS2). In other words, a radiation receiving component can be arranged to receive the first feedback electromagnetic signal (FS1) and the second feedback electromagnetic signal (FS2).

In step S103, the first feedback electromagnetic signal (FS1) and the second feedback electromagnetic signal (FS2) can be analyzed by coupling the radiative emission components 11 and 12 with a computing component. More specifically, the first feedback electromagnetic signal (FS1) and the second feedback electromagnetic signal (FS2) can be converted into electrical signals for signal analysis. An implementable signal analysis may be, for example, a spectrum analysis, a main frequency analysis, an amplitude analysis, a peak time analysis, or a method of analyzing the time, frequency, and/or amplitude of a signal. It should be noted that in step S103, it is not necessary to converting the first feedback electromagnetic signal (FS1) and the second feedback electromagnetic signal (FS2) into electrical signals. More specifically, the conversions of the first feedback electromagnetic signal (FS1) and the second feedback electromagnetic signal (FS2) will be performed based on the computing components. Particularly, directly using computing component that can analyze electromagnetic signals with convert the first feedback electromagnetic signal (FS1) and the second feedback electromagnetic signal (FS2). The computing component may be selected from an Application Specific Integrated Circuit (ASIC), a FPGA, a microprocessor, a computer, a spectrum analyzer, an oscilloscope, or other components with signal analysis capabilities.

Figure 3:
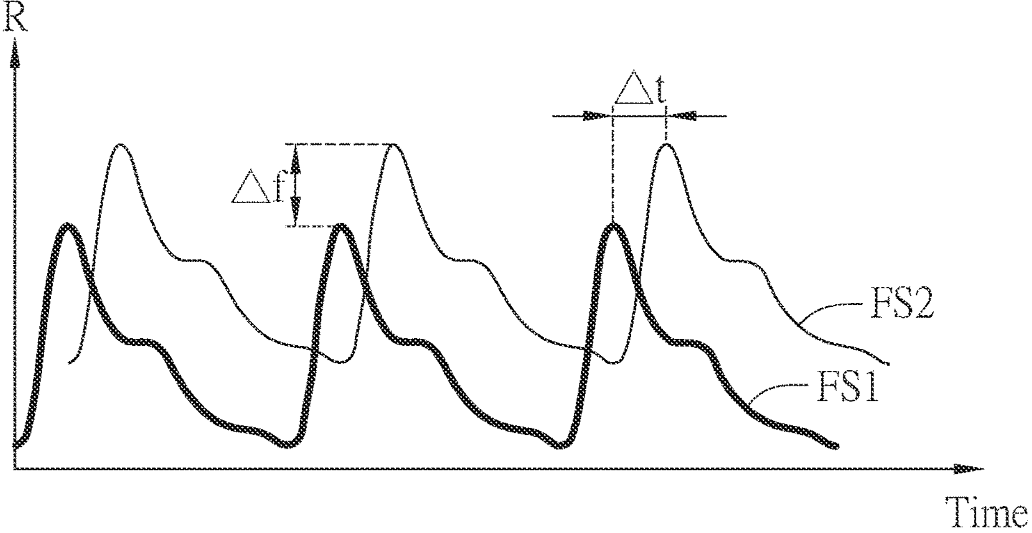
FIG. 3 is a schematic diagram of the measurement results of the method for measuring vascular state according to the first embodiment of the present disclosure.

In step S104, the computing component calculates the at least one vascular state of the target vessel (TV) based on the difference in the signal characteristics between the first feedback electromagnetic signal (FS1) and the second feedback electromagnetic signal (FS2). The vascular state includes a vascular embolism (located between the first detecting location (DL1) and the second detecting location (DL2)), a vascular sclerosis, a pulse transmission velocity, and an evaluation of blood flow velocity. For example, as shown in FIG. 3, X-axis represents time or time-dependent data (e.g. the Nth data), and the Y-axis represents the response R, which regards the measurable numerical result caused by the first feedback electromagnetic signal (FS1) and the second feedback electromagnetic signal (FS2). The measured numerical result can be amplitude, frequency, frequency change, inductance value, inductance change, or other signal or hardware parameters. By measuring the frequency difference between the first feedback electromagnetic signal (FS1) and the second feedback electromagnetic signal (FS2) due to the eddy currents (11) and (12) Δf, the vascular embolism can be determined/evaluated based on the frequency differences Δf. More specifically, experimental methods such as big data or simulation experiments may be used to identify the relationship/correlation between the frequency differences Δf and the level of vascular embolism through building table or other data comparison methods. When the frequency differences Δf is detected, the information on the level of the vascular embolism can be provided by comparing the frequency differences Δf and the data base. On the other hand, the distance D between the first detecting location (DL1) and the second detecting location (DL2), and the time delay Δt between the first feedback electromagnetic signal (FS1) and the second feedback electromagnetic signal (FS2) can be used to calculate the PWV. More specifically, the PWV can be evaluated using the following formula:

$$PWV \cong \frac{D}{\Delta t}$$

A pulse on vessels related to the contraction and relaxation transmission of blood is produced by the heart pumping blood in the vessels. When the level of hardening of the blood vessels is higher, it is often accompanied by a higher PWV. Therefore, the level of hardening of the target vessel (TV) can be evaluated through the PWV. It should be noted that the above application examples are only used to exemplarily illustrate the calculations of the vascular states of the present disclosure and are not intended to limit the present invention. Moreover, the calculations of the vascular states of the present disclosure can be supplemented with parameters such as a heart rate, a blood pressure, the ages of the cognitive, or other parameters for correction to make the evaluation/calculation of the vascular state more accurate. Moreover, in the present disclosure, the vascular state of the target vessel (TV) can also be evaluated by comparing the various parameters of the past and current target vessel (TV) through a long-term measurement to a subject.

It should be noted that the present invention is not limited to the type and location of the target vessel (TV). The target vessel (TV) can be any large blood vessel (preferably an artery) on a human body or an experimental subject (e.g. animals). In an embodiment, the target vessel (TV) is, preferably, the cervical artery for a long-term observation. With the long-term observation of the vascular state of the neck arteries, the risk of stroke or other fatal diseases in the subject can be evaluated or determined.

Second Embodiment

Figure 4:
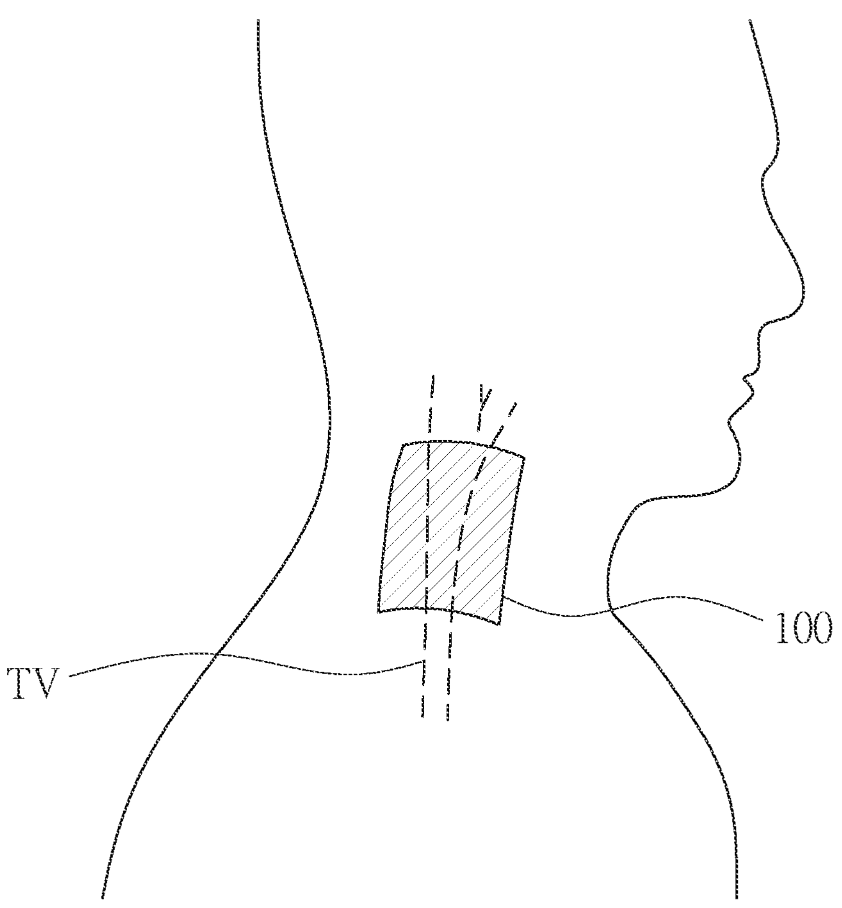
FIG. 4 is a schematic diagram of an adhesive vascular state measurement device attached to the neck according to the second embodiment of the present disclosure.

In the second embodiment, disclosing an exemplary device for applying the method for measuring vascular state 10 of the first embodiment. It should be noted that the implementation of the method for measuring vascular state 10 is not limited to the device of the second embodiment. Referring FIGS. 4 and 5, the adhesive vascular state measurement device 100 comprises a flexible substrate 110, a first coil 120, a second coil 130 and a control module 140.

The flexible substrate 110 is attached on a skin surface along a target vessel (TV). The first coil 120 is arranged at a first position (L1) of the flexible substrate 110. The first coil 120 is configured to output a first transmission electromagnetic signal (TS1) toward a first detecting location (DL1) of the target vessel (TV), and receive a first feedback electromagnetic signal (FS1) induced, at the first detecting location (DL1), by the first transmission electromagnetic signal (TS1) to generate a first sensing signal (SS1). The second coil 130 is arranged at a second position (L2) of the flexible substrate 110. The second coil 130 is configured to output a second transmission electromagnetic signal (TS2) toward a second detecting location of the target vessel (TV), and receive a second feedback electromagnetic signal (FS2) induced, at the second detecting location, by the second transmission electromagnetic signal (TS2) to generate a second sensing signal ((SS2)). The control module 140 is coupled with the first coil 120 and the second coil 130. The control module 140 includes a signal generating unit 141 and a measurement unit 142. The signal generating unit 141 is configured to generate an AC signal (AS) provided to the first coil 120 and the second coil 130 to generate the first transmission electromagnetic signal (TS1) and the second transmission electromagnetic signal (TS2), respectively. The measurement unit 142 is configured to receive the first sensing signal (SS1) and the second sensing signal ((SS2)), and determine at least one vascular state of the target vessel (TV) according to a signal characteristic difference between the first sensing signal (SS1) and the second sensing signal ((SS2)).

More specifically, the flexible substrate 110 may be a thin film material such as a polyimide film (PI Film) or a polyester resin film (PET Film). The size and softness of the flexible substrate 110 may be adjusted to be suitable for being arranged on the skin surface over the target vessel (TV). For example, when the target vessel (TV) includes a cervical artery, the flexible substrate 110 will be disposed on the neck of the subject. Hence, the length and width of the flexible substrate 110 should be adjusted to be appropriately set on the neck. The flexible substrate 110 can be attached by any conventional adhesion methods such as static electricity, adhesive, or tape. The flexible substrate 110 provides users with a more comfortable wearing method without affect the mobility of the users, which is beneficial to long-term wearing or home wearing. In an embodiment, the side of the flexible substrate 110 attached to the skin may be integrated with a matching layer. The matching layer may be selected from materials with a magnetic impedance in a range of the magnetic impedance of the skin, the magnetic impedance of the flexible substrate 110, or the magnetic impedance of the medium. Accordingly, the matching layer will reduce the energy loss during transferring the first transmission electromagnetic signal (TS1) and the second transmission electromagnetic signal (TS2). Therefore, the matching layer will achieve the goal of measuring the required depth or improving the signal-to-noise ratio with a smaller energy.

The first coil 120 and the second coil 130 are arranged on the flexible substrate 110, for example, a conductive wire can be arranged on the flexible substrate 110 to form the first coil 120 and the second coil 130. More specifically, the conductive wire formed on the flexible substrate 110 can be formed by conventional manufacturing techniques such as etching, engraving, and photolithography. The conductive wire has parts corresponding to the first coil 120 and the second coil 130 to emit the first transmission electromagnetic signal (TS1) and the second transmission electromagnetic signal (TS2). The present disclosure is not limited to the example of the first coil 120 and the second coil 130. For example, the first coil 120 and the second coil 130 can be, but not limited to, a single turn coil, a multi-turn coil, or a helical coil. In addition, the first coil 120 and/or the second coil 130 can be planar coils, for example, forming conducting wire on one layer of the substrate. On the other hand, the coil on the flexible substrate 110 can also be a three-dimensional coil, for example, forming a coil pattern with a conductive wire of at least two layers on the flexible substrate 110. By using a conventional circuit manufacturing method to produce the first coil 120 and the second coil 130, the yield and consistency of the first coil 120 and the second coil 130 can be effectively improved. Furthermore, the first coil 120 and the second coil 130 can be easily integrated with other circuit components and modules. Alternatively, the first coil 120 and the second coil 130 can be a separate component instead of being arranged on a substrate. For example, the first coil 120 and/or the second coil 130 can be a coil wound with enameled wire (for example only, not to limit the material of the coils). The types of the first coil 120 and the second coil 130 can be selected from different radiation parts, materials, turns, shapes, etc. according to the purpose.

Figure 5:
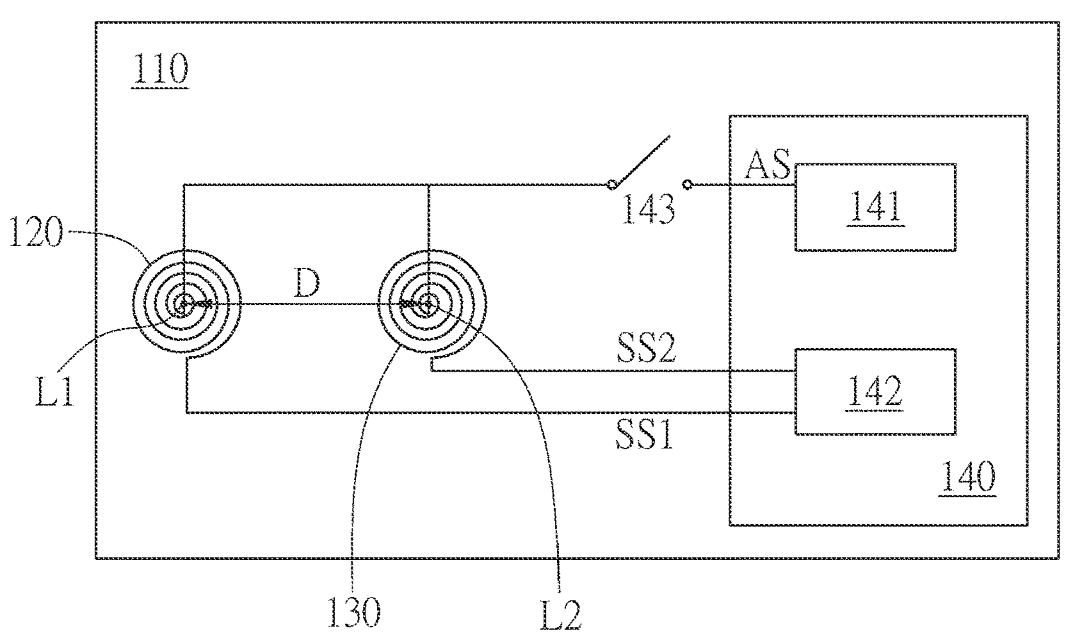
FIG. 5 is a block diagram of an adhesive vascular state measurement device according to the second embodiment of the present disclosure.
Figure 6:
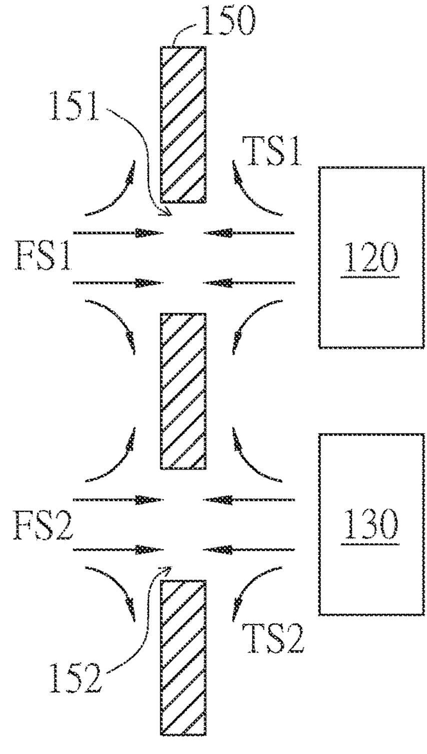
FIG. 6 is a schematic diagram of the function of the isolation layer according to the second embodiment of the present disclosure.

It should be noted that the first position (L1) and second position (L2) in FIG. 5 are only illustrative and not intended to limit the present invention. For example, the first position (L1) and the second position (L2) can be adjusted according to the size of the flexible substrate 110 or the arranging direction of the flexible substrate 110 on the skin. The arrangement of the first position (L1) and the second position (L2) corresponds to the blood flow direction and/or an extending direction of the target vessel (TV).

The control module 140 is coupled to the first coil 120 and the second coil 130. For example, the control module 140 can be an independent module coupled to the first coil 120 and the second coil 130, respectively. For example, an independent control module 140 can be a programmable or an instrument-controlled module or device such as a computer, a tablet, an industrial computer, an instrument, FPGA, a microprocessor, etc. The independent control module 140 may be chosen from control modules with different computing capabilities according to requirements. Therefore, for instance, when a high computing capability or a high level of regulatory/safety requirements need to be met, a component with advanced computing capability can be selected as the control modules 120. On the contrary, the control module 140 may be integrated with the first coil 120 and second coil 130 onto the flexible substrate 110. For example, when the device is required to be lightweight and easy to carry, a highly integrated component such as system on a chip (SOC) or application specific integrated circuit (ASIC) can be selected as the control modules 140. Integrating control module 140, the first coil 120, and the second coil 130 through conducting wires formed on the flexible substrate 110 can reduce the physical lines for communication or signal connections to achieve the objects that making the subject's movement less restricted and easier to be wore for a long time.

The signal generating unit 141 can be an AC/DC signal generator composed by active components (such as oscillators, and/or timers) and/or passive components (such as resistors, capacitors, and/or inductors). For example, the signal generating unit 130 may be configured to directly generate the excitation signal provided to the first coil 110. On the other hand, the signal generating unit 130 may be configured to convert DC signals into the excitation signal. More specifically, the signal generating unit 130 may include a DC supply source and a resonant circuit. The resonant circuit receives the DC signal provided by the DC supply source to generate the excitation signal. By using a DC signal source and a resonant circuit to generate the excitation signal. Because the resonant circuit only requires a series/parallel combination of passive components (such as the resistor R, the capacitor C, the inductor L), the desired effect for generating the excitation signal will be achieved by simple circuit with low energy consumption. In this embodiment, the signal generating unit 130 is preferred to provide a square wave signal. In the embodiment, the frequency of the AC signal (AS) of the signal generating unit 141 is, preferably, in a range of 1-10 MHz. Therefore, the resonant frequency range of the resonant circuit is, preferably, in a range of 1-10 MHz.

After the signal generating unit 141 provides an AC signal (AS) to the first coil 120 and the second coil 130, the first coil 120 and the second coil 130 generate the first transmission electromagnetic signal (TS1) and the second transmission electromagnetic signal (TS2) due to the electromagnetic effects. The first coil 120 and the second coil 130 output, respectively, the first transmission electromagnetic signal (TS1) and the second transmission electromagnetic signal (TS2) to the first detecting location (DL1) and the second detecting location (DL2) of the target vessel (TV). The eddy currents (11) and (12) are generated at the first detecting location (DL1) and the second detecting location (DL2), respectively. The eddy currents (11) and (12) will generate the first feedback electromagnetic signal (FS1) and the second feedback electromagnetic signal (FS2), respectively. The first coil 120 will receive the first feedback electromagnetic signal (FS1), and the second coil 130 will receive the second feedback electromagnetic signal (FS2). The first feedback electromagnetic signal (FS1) and the second feedback electromagnetic signal (FS2) will be converted, by the first coil 120 and the second coil 130 respectively, to the first sensing signal (SS1) and the second sensing signal ((SS2)) due to the magnetoelectric effect.

The measurement unit 142 of the control module 140 can perform signal analysis on the first sensing signal (SS1) and the second sensing signal (SS2) to obtain the frequency, amplitude, or other signal parameters of the first sensing signal (SS1) and the second sensing signal (SS2). According to signal parameters, the measurement unit 142 can analyze the signal characteristic differences of the first sensing signal (SS1) and the second sensing signal (SS2) according to the method in the first embodiment. The vascular state information of the target vessel (TV) can be determined by the measurement unit 142 according to the difference in signal characteristics.

In the embodiment, the first coil 120 is arranged at the first position (L1) of the flexible substrate 110, and the second coil 130 is arranged at the second position (L2) of the flexible substrate 110. The preset distance between the first position (L1) and the second position (L2) can be used to estimate the distance between the first detecting location (DL1) and the second detecting location (DL2) (for example, equal to or slightly equal to). Therefore, the preset distance between the first position (L1) and the second position (L2) can also be used to calculate the PWV by considering the delay time of the first sensing signal (SS1) and the second sensing signal (SS2).

In the embodiment, the control module 140 may further include a switching unit 143, which is coupled to the output of the signal generating unit 141. When the measurement unit 142 receives the first sensing signal (SS1) and the second sensing signal (SS2), the signal generating unit 141 is disabled, by the switch unit 143, to output the AC signal (AS). More specifically, the switching unit 143 can switch the output of signal generating unit 141. When it is necessary to output the first transmission electromagnetic signal (TS1) and the second transmission electromagnetic signal (TS2), the switching unit 143 opens the output of signal generating unit 141 to connect the first coil 120 and the second coil 130. When the measurement unit 142 receives the first sensing signal (SS1) and the second sensing signal (SS2), the output of the signal generating unit 141 will be turned off or grounded by the switching unit 143. Therefore, the signal generating unit 141 is disabled, so that the first coil 120 and the second coil 130 will not receive the AC signal (AS). The measurement unit 142 will receive the first sensing signal (SS1) and the second sensing signal (SS2) without being affected by the AC signal (AS). However, it should be noted that the present invention is not limited to the scenario of receiving the first sensing signal (SS1) and the second sensing signal (SS2) mentioned above. More specifically, in the present disclosure, it is also possible that receiving, by the measurement unit 142, the first sensing signal (SS1) and the second sensing signal (SS2) while the first coil 120 and the second coil 130 emitting the first transmission electromagnetic signal (TS1) and the second transmission electromagnetic signal (TS2). At this time, the measurement unit 142 can measure the inductance value changes of the first coil 120 and/or the second coil 130 caused by the mutual cancellation of electromagnetic signals to estimate the first sensing signal (SS1) and the second sensing signal (SS2).

In an embodiment, the adhesive vascular state measurement device 100 further comprises an isolation layer 150 arranged between the flexible substrate 110 and the skin of the subject. The isolation layer 150 has gaps 151 and 152 corresponding to the first coil 120 and the second coil 130, respectively. The gaps 151 and 152 of the isolation layer 150 is configured to make the first transmission electromagnetic signal (TS1) and the second transmission electromagnetic signal (TS2) emitted by the first coil 120 and the second coil 130 more directional and less to affect each other. With the isolation layer 150, the signal quality will be improved, and the resolution for the first detecting location (DL1) and the second detecting location (DL2) can also be improved.

In an embodiment, the control module 140 of the adhesive vascular state measurement device 100 further comprises a communication unit. The communication unit is configured to transmit the vascular state information to an electronic device through the communication unit. More specifically, examples of the electronic devices include a smartphone, a desktop, a laptop, and other backend devices. The communication unit communicates with the electronic device through wireless protocol (e.g. Bluetooth, wireless network, infrared, etc.) or wired protocol (e.g. a wired network or cable, etc.) and provides the at least one vascular state information to the electronic device. Application programs can be installed inside the electronic device to record or analyze the at least one vascular state information. With the communication unit, it is possible to achieve long-term tracking of the vascular state of the subjects and evaluate the risk of cardiovascular diseases or stroke based on the at least one vascular state information provided to the backend device, which is tracked for vascular state changes over the long-term.

Through the adhesive vascular state measurement device 100 mentioned above, it is possible to attach it to the skin of the subject and directly emit two sets of electromagnetic signals to two detecting locations of the target vessel (TV), and receive feedback electromagnetic signals generated at the two detecting locations of the target vessel (TV). By comparing the signal differences of the two feedback electromagnetic signals at the two detecting locations of the target vessel (TV), the vascular state between the two detecting locations of the target vessel (TV) can be estimated. Besides, by using the flexible substrate 110 and the conventional producing procedure of the circuit technology, the cost of the adhesive vascular state measurement device 100 can be significantly reduced, and the volume of the device can also be reduced or miniaturized. Therefore, the convenience and comfort of portability and wearing of the adhesive vascular state measurement device 100 will be significantly improved comparing to the conventional devices. Therefore, the object of detecting in real-time or long-term monitoring of the vascular state can be achieved.

The previous description of the present disclosure is provided to enable a person of ordinary skill in the art to make or implement the present invention. Various modifications to the present invention will be apparent to a person skilled in the art, and the general principles defined herein can be applied to other variations without departing from the spirit or scope of the present disclosure. Therefore, the present invention is not intended to be limited to the examples described herein, but is to be in accord with the widest scope consistent with the principles and novel features of the invention herein.

What is claimed is:

1. An adhesive vascular state measurement device comprising:

a flexible substrate for being attached on a skin surface along a target vessel;

a first coil arranged at a first position of the flexible substrate; wherein the first coil is configured to output a first transmission electromagnetic signal toward a first detecting location of the target vessel, and receive a first feedback electromagnetic signal induced, at the first detecting location, by the first transmission electromagnetic signal to generate a first sensing signal;

a second coil arranged at a second position of the flexible substrate; wherein the second coil is configured to output a second transmission electromagnetic signal toward a second detecting location of the target vessel, and receive a second feedback electromagnetic signal induced, at the second detecting location, by the second transmission electromagnetic signal to generate a second sensing signal, wherein the first coil and the second coil are arranged in a line along an extending direction of the target vessel; and a control module coupled with the first coil and the second coil, wherein the control module includes:

a signal generating unit configured to generate an AC signal provided to the first coil and the second coil to generate the first transmission electromagnetic signal and the second transmission electromagnetic signal, respectively; and a measurement unit configured to receive the first sensing signal and the second sensing signal, determine a signal characteristic difference between the first sensing signal and the second sensing signal that are derived substantially simultaneously from different locations along the extending direction, and determine at least one vascular state of the target vessel according to the signal characteristic difference.

2. The adhesive vascular state measurement device of claim 1, wherein the signal characteristic difference at least includes a frequency difference between the first sensing signal and the second sensing signal.

3. The adhesive vascular state measurement device of claim 1, wherein the signal characteristic difference at least includes a delay time between the first sensing signal and second sensing signal.

4. The adhesive vascular state measurement device of claim 3, wherein a preset distance is existed between the first position and the second position; wherein the measurement unit determines, according to the delay time and the preset distance, an evaluated blood flow velocity between the first detecting location and the second detecting location.

5. The adhesive vascular state measurement device of claim 1, wherein the control module further includes a switch unit coupled to the output of the signal generating unit; when the measurement unit is receiving the first sensing signal and the second sensing signal, the signal generating unit is disabled, by the switch unit, to output the AC signal.

6. The adhesive vascular state measurement device of claim 1, wherein the target vessel includes a carotid artery, and the flexible substrate is configured to attach on a neck skin.

7. The adhesive vascular state measurement device of claim 1, wherein the at least one vascular state includes a level of embolism between the first detecting location and the second detecting location of the target vessel and a level of hardening of the target vessel.

8. A method for measuring vascular state, comprising:

applying the adhesive vascular state measurement device of claim 1 to a target vessel;

outputting the first transmission electromagnetic signal to the first detecting location of the target vessel, and outputting the second transmission electromagnetic signal to the second detecting location of the target vessel;

receiving the first feedback electromagnetic signal induced, at the first detecting location, by the first transmission electromagnetic signal to generate the first sensing signal, and receiving the second feedback electromagnetic signal induced, at the second detecting location, by the second transmission electromagnetic signal to generate the second sensing signal;

determining the signal characteristic difference between the first sensing signal and the second sensing signal; and determining the at least one vascular state of the target vessel according to the signal characteristic difference.

9. The method of claim 8, wherein determining the signal characteristic difference at least includes determining a frequency difference between the first sensing signal and the second sensing signal.

10. The method of claim 8, wherein determining the signal characteristic difference at least includes determining a delay time between the first sensing signal and second sensing signal.

11. The method of claim 10 further comprising:

determining an evaluated blood flow velocity between the first detecting location and the second detecting location according to the delay time and a distance between the first detecting location and the second detecting location.

12. The method of claim 8, wherein the target vessel includes a carotid artery, and the flexible substrate is configured to attach on a neck skin.

13. The method of claim 8, wherein the at least one vascular state includes a level of embolism between the first detecting location and the second detecting location of the target vessel and a level of hardening of the target vessel.

* * * * *